United States Patent [19]

Keimel

[11] Patent Number: 5,383,909
[45] Date of Patent: Jan. 24, 1995

[54] DIAGNOSTIC TELEMETRY SYSTEM FOR AN APPARATUS FOR DETECTION AND TREATMENT OF TACHYCARDIA AND FIBRILLATION

[75] Inventor: John G. Keimel, New Brighton, Minn.

[73] Assignee: Medtronic, Inc., Minneapolis, Minn.

[21] Appl. No.: 10,970

[22] Filed: Jan. 29, 1993

[51] Int. Cl.[6] .............................................. A61N 1/39
[52] U.S. Cl. .......................................... 607/7; 607/32
[58] Field of Search .................... 607/5, 7, 14, 30, 31, 607/32

[56] References Cited

U.S. PATENT DOCUMENTS

| | | | |
|---|---|---|---|
| 4,223,678 | 9/1980 | Langer | 607/9 |
| 4,374,382 | 2/1983 | Markowitz | 340/870.01 |
| 4,375,817 | 3/1983 | Engle | 607/5 |
| 4,548,209 | 10/1985 | Wielders | 607/27 |
| 4,577,633 | 3/1986 | Berkovits | 607/15 |
| 4,587,970 | 5/1986 | Holley | 607/15 |
| 4,625,730 | 12/1986 | Fountain et al. | 607/32 |
| 4,693,253 | 9/1987 | Adams | 607/4 |
| 4,726,380 | 2/1988 | Vollmann | 607/15 |
| 4,800,883 | 1/1989 | Winstrom | 607/7 |
| 4,880,005 | 11/1989 | Pless | 607/15 |
| 4,949,719 | 8/1990 | Pless | 607/7 |
| 4,953,551 | 9/1990 | Mehra | 607/5 |
| 4,969,465 | 11/1990 | Pless | 607/4 |
| 4,971,058 | 11/1990 | Pless | 607/4 |
| 5,063,928 | 11/1991 | Grevis | 607/14 |
| 5,117,824 | 6/1992 | Keimel | 607/4 |
| 5,127,404 | 7/1992 | Wyborny | 607/2 |
| 5,163,427 | 11/1992 | Keimel | 607/2 |
| 5,205,283 | 4/1993 | Olson | 607/5 |

OTHER PUBLICATIONS

"Onset and Stability for Ventricular Tachyarrhythmia Detection in an Implantable Pacer-Cardioverter-Defibrillator" by Walter H. Olson et al. in Computers in Cardiology, 1986, pp. 167–170.

Primary Examiner—George Manuel
Attorney, Agent, or Firm—Reed A. Duthler; Harold R. Patton

[57] ABSTRACT

An implantable antitachyarrhythmia device having the capability of detecting multiple tachyarrhythmias, such as ventricular tachycardia and ventricular fibrillation and capable of delivering multiple therapies, such as antitachycardia pacing, cardioversion and defibrillation. In order to assist the physician in understanding the progress of the device toward detecting a tachyarrhythmia and to better understand the operation of the therapy provided by the device, the device transmits information related to these functions on a beat by beat basis, as a supplement to marker signals associated with paced and sensed heart events. The information telemetry regarding detection allows the physician to determine how the particular R—R interval preceding the telemetry has effected the internal counts or other diagnostic parameters required to accomplish tachyarrhythmia detection. Similarly, in conjunction with stimulus pulses, the device transmits information indicative of which of the available therapy regimens is presently in effect.

12 Claims, 9 Drawing Sheets

Marker Codes

| MARKER TYPE | LSB+7...LSB | HEX |
|---|---|---|
| Ventricular sense | 0000 0000 | 00 |
| Ventricular refractory sense | 1000 0010 | 82 |
| Ventricular pace | 1000 0100 | 84 |
| Ventricular fibrillation sense | 0000 0110 | 06 |
| Ventricular tachy sense (slow) | 1000 1000 | 88 |
| Ventricular tachy sense (fast via VT) | 0010 0010 | 22 |
| Ventricular tachy sense (fast via VF) | 1010 1010 | AA |
| Ventricular cardioversion/defibrillation pulse | 0000 1010 | 0A |
| Ventricular tachy detection (slow) complete | 1010 0000 | A0 |
| Ventricular tachy detection (fast) complete | 0010 0100 | 24 |
| Ventricular fibrillation detection complete | 1010 0110 | A6 |
| Atrial sense | 1100 0000 | C0 |
| Atrial refractory sense | 0100 0010 | 42 |
| Atrial pace | 0100 0100 | 44 |
| Atrial fibrillation sense | 1100 0110 | C6 |
| Atrial tachy sense | 0100 1000 | 48 |
| Atrial cardioversion/defibrillation pulse | 1100 1010 | CA |
| Atrial tachy detection complete | 0110 0000 | 60 |
| Atrial fibrillation detection complete | 0110 0110 | 66 |
| Capacitor charging ended | 0000 1100 | 0C |
| Data/Null | 0010 1000 | 28 |

Marker Supplement Byte 1
MSB...LSB

| Bits | Description |
|---|---|
| 10 XX XX XX<br>11 XX XX XX<br>01 XX XX XX | Device is in Magnet State (Reed Switch Closed, Detection Suspended)<br>Device is in Cancel Magnet State (Reed Switch closed)<br>Device is in Permanent Telemetry State (Reed Switch is Open) |
| XX 0X XX XX<br>XX 1X XX XX | No episode is in progress<br>Episode is in progress |
| XX X0 XX XX<br>XX X1 XX XX | No detected VT, FVT, or VF episodes since last cleared<br>VT, FVT, or VF episode termination detected since last cleared 1 |
| XX XX 00<br>XX XX 01<br>XX XX 10<br>XX XX 11 | VT Event Count last reset by other than Onset, Stability, or EGM Width<br>VT Event Count was last reset by Onset Criterion<br>VT Event Count was last reset by Stability Criterion<br>VT Event Count was last reset by EGM Width Criterion |

FIG.4b

| Marker Supplement Byte 2 MSB...LSB | |
|---|---|
| 0 0000000 | VF Event Count = 0 |
| 0 0000001 | VF Event Count = 1 |
| ... | ... |
| 0 0011110 | VF Event Count = 30 |
| 1 0 XXXXXX | Charging is not in progress |
| 1 1 XXXXXX | Charging is in progress |
| 1 X 000000 | Slow VT Therapy #1 is in progress |
| ... | ... |
| 1 X 000101 | Slow VT Therapy #6 is in progress |
| 1 X 000110 | Fast VT Therapy #1 is in progress |
| ... | ... |
| 1 X 001011 | Fast VT Therapy #6 is in progress |
| 1 X 001100 | VF Therapy #1 is in progress |
| ... | ... |
| 1 X 010001 | VF Therapy #6 is in progress |
| 1 X 010010 | Triggered Temporary is in progress (reference 4.1.5) |
| 1 X 010011 | Reed Switch Close Therapy is in progress |
| 1 X 010100 | Automatic Capacitor Charging is in progress |

FIG. 4c

| Marker Supplement Byte 3 MSB...LSB | |
|---|---|
| 0 0000000 | VT Event Count = 0 |
| 0 0000001 | VT Event Count = 1 |
| ... | ... |
| 0 0110100 | VT Event Count = 52 |
| 1 0000000 | Therapy Scan #1 in progress |
| ... | ... |
| 1 0011111 | Therapy Scan #31 in progress |

FIG.4d

| Marker Supplement Byte 4 MSB...LSB | N* (328,000 / 32,768) mS |
|---|---|
| 00001100 | Cardiac interval is 120 mS |
| 00001101 | Cardiac interval is 130 mS |
| ... | ... |
| 11001000 | Cardiac interval is 2000 mS |
| 11001001 | Cardiac interval is > 2000 mS |

FIG.4e

| Marker Supplement Byte 5 | |
|---|---|
| MSB...LSB | |
| 0 0XXXXXX<br>0 1XXXXXX | All VF Therapies are programmed OFF<br>At least one VF Therapy is programmed ON |
| 0 X0XXXXX<br>0 X1XXXXX | All Fast VT Therapies are programmed OFF<br>At least one Fast VT Therapy is programmed ON |
| 0 XX0XXXX<br>0 XX1XXXX | All Slow VT Therapies are programmed OFF<br>At least one Slow VT Therapy is programmed ON |
| 0 XXX0XXX<br>0 XXX1XXX | VF Detection is OFF<br>VF Detection is ON |
| 0 XXXX0XX<br>0 XXXX1XX | Fast VT Detection via VF is programmed OFF<br>Fast VT Detection via VF is programmed ON |
| 0 XXXXX0X<br>0 XXXXX1X | Fast VT Detection via VT is programmed OFF<br>Fast VT Detection via VT is programmed ON |
| 0 XXXXXX0<br>0 XXXXXX1 | VT Detection is OFF<br>VT Detection is ON |
| 1 0 XXXXXX<br>1 1 XXXXXX | EGM width was greater than programmed threshold<br>EGM width was less than programmed threshold |
| 1 X 000001<br>1 X 000010 | EGM width is 1 sample (3.906 mS @ 256 Hz)<br>EGM width is 2 samples (7.813 mS @ 256 Hz) |
| 1 X 110010 | EGM width is 50 samples (195.3 mS @ 256 Hz) |

DIAGNOSTIC TELEMETRY SYSTEM FOR AN APPARATUS FOR DETECTION AND TREATMENT OF TACHYCARDIA AND FIBRILLATION

BACKGROUND OF THE INVENTION

This invention relates to implantable devices which detect and/or treat tachyarrhythmias and more specifically to telemetry systems employed in such devices to transmit information to an external receiver to assist the physician in monitoring and understanding the operation of the devices.

In pacemaker/cardioverter/defibrillators presently in clinical evaluation, ventricular fibrillation and ventricular tachycardias are identified using rate based criteria. In such devices, it is common to specify rate or interval ranges that characterize one or more types of ventricular tachycardias and fibrillation. Counts of the measured R—R intervals which fall into the rate ranges are used to determine whether a tachyarrhythmia is present and to diagnose the particular tachyarrhythmia. The detection methodologies practiced in such devices may be difficult for the physician to follow, as the individual intervals may increment or not increment an individual count depending on factors other than the interval duration alone. For example, rapid onset criteria based on preceding intervals may be required to initiate counting and stability criteria based on the preceding intervals may be required to continue counting. In some devices, whether a measured R—R interval increments a count and which count is incremented may be a function of both the individual interval duration and the average rate over the preceding series of intervals. Patents illustrative of such detection methodologies include U.S. Pat. Nos. 4,830,006, 4,969,465 and 5,063,928.

In implantable anti-tachyarrhythmia devices, each of the possible diagnoses provided by the device will trigger a predefined therapy, with the general aggressiveness of the therapies increasing from least aggressive if the diagnosis is a slow ventricular tachycardia to most aggressive if the diagnosis is ventricular fibrillation. For example, anti-tachycardia pacing may be employed in response to a diagnosis of slow ventricular tachycardia, cardioversion may be employed if the diagnosis is fast ventricular tachycardia and defibrillation may be employed if the diagnosis is fibrillation.

Most currently available devices of the type in which the present invention may be practiced provide for a menu of available therapies for each type of tachyarrhythmia diagnosed. In programming such devices it is typical to specify a number of different therapies for each diagnosed tachyarrhythmia, with therapies attempted sequentially in response to the failure of a previous therapy to terminate the arrhythmia. The sequence of therapies actually delivered in such devices may also be difficult for the physician to follow, as the sequence may depend not only on the particular arrhythmia presently diagnosed, but on the success or failure of preceding therapies delivered in response to previously detected arrhythmias and/or on whether the rhythm has accelerated or decelerated during delivery of a preceding therapy. Patents illustrating such therapy delivery schedules and menus include U.S. Pat. Nos. 4,830,006, 4,969,465 and 5,063,928, referred to above.

Presently available implantable anti-tachyarrhythmia devices typically also include provision for storage of diagnostic information such as the numbers and types of arrhythmias detected and of the therapies delivered. Some devices, such as the Medtronic Model 7216 and 7217 implantable pacemaker/cardioverter/defibrillators also have the capability to transmit marker channel information in conjunction with each sensed R-wave. This information may indicate which interval range the interval ending with the sensed R-wave falls into, based on the programmed criteria for identifying the various tachyarrhythmias. Other devices include the ability to store and transmit segments of recorded ECG associated with the detection of arrhythmias and/or the delivery of anti-tachyarrhythmia therapies. Patents disclosing such diagnostic telemetry systems include U.S. Pat. Nos. 4,295,474, 4,223,678 and U.S. Pat. No. 4,567,883.

Recently, a new telemetry format for implantable devices has been developed, which allows for transmission of analog and digital information in more compact form, as disclosed in U.S. Pat. No. 5,127,404, issued to Wyborny et al., incorporated herein by reference in its entirety. This telemetry format employs pulse position modulation to encode data in hexadecimal form rather than binary form, dramatically reducing the time required to transmit substantial blocks of information.

SUMMARY OF THE INVENTION

The present invention provides a telemetry system which assists the physician in following the operation of an implantable anti-tachycardia device, both during detection of tachyarrhythmias and during delivery of anti-tachyarrhythmia therapies. This result is accomplished by transmitting supplemental information with regard to the device's current arrhythmia detection and anti-tachycardia therapy delivery status on a beat by beat basis, following individual detected R-waves or delivered therapy pulses. In the preferred embodiment of the invention, the status information is transmitted as a supplement to transmission of markers as discussed above, indicating the type of interval ending with the R-wave sensed. In the disclosed embodiment of the invention, the arrhythmia detection criteria correspond to those disclosed in U.S. patent application No. 08/010,920, by Keimel, for a "Method and Apparatus for Detection and Treatment of Tachycardia and Fibrillation", filed as of the date of the present application by Keimel et al., incorporated herein by reference in its entirety. The therapy schedule and therapy menu correspond generally to those of the Medtronic Model 7216 and 7217 implantable pacemaker/cardioverter/defibrillators and the transmission of the status data is accomplished using the improved telemetry format disclosed in the above-cited Wyborny et al. patent. However, the invention is believed to generally be practicable in conjunction with any devices of the types disclosed in the above cited references.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENT

Figure 1:
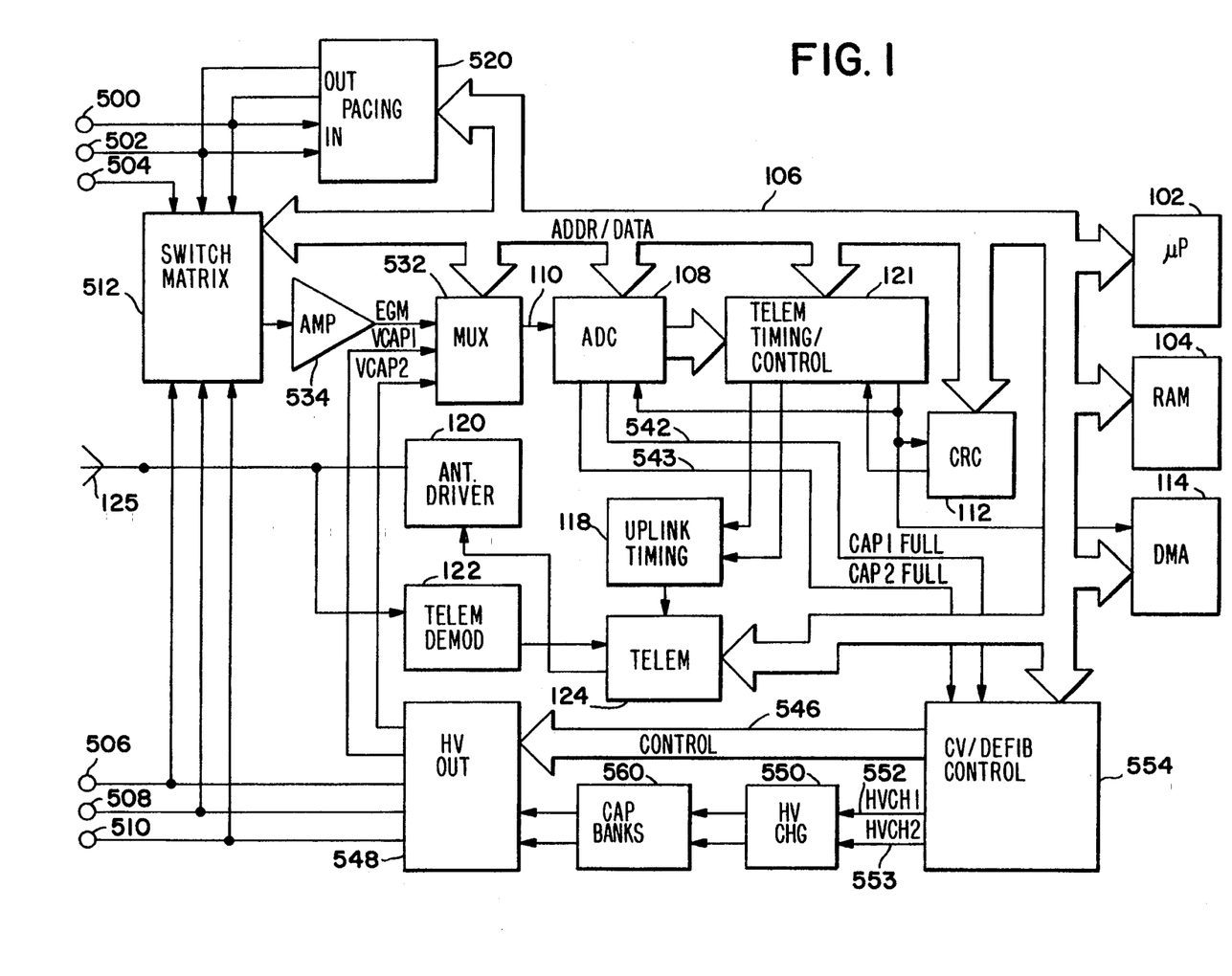
FIG. 1 is a simplified block diagram illustrating the components of a device within which the method and apparatus of the present invention may be implemented.

FIG. 1 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator/cardioverters presently being implanted for clinical evaluation in the United States. The invention is also believed practicable in conjunction with implantable pacemaker/cardioverters/defibrillators as disclosed in prior U.S. Pat. No. 4,548,209, issued to Wielders, et al. on Oct. 22, 1985, U.S. Pat. No. 4,693,253, issued to Adams et al. on Sep. 15, 1987, U.S. Pat. No. 4,830,006, issued to Haluska et al. on May 6, 1989 and U.S. Pat. No. 4,949,730, issued to Pless et al. on Aug. 21, 1990, all of which are incorporated herein by reference in their entireties.

The device is illustrated as being provided with six electrodes, 500, 502, 504, 506, 508 and 510. Electrodes 500 and 502 may be a pair of endocardial electrodes located in the ventricle, mounted to a tranvenous lead. Electrode 504 may be located on or may be part of the housing of the implantable pacemaker/cardioverter/defibrillator. Electrodes 506, 508 and 510 may be large surface area defibrillation electrodes located in the ventricle, coronary sinus, superior vena cava or may be subcutaneous or epicardial defibrillation electrodes.

Electrodes 500 and 502 are shown as hard-wired to the inputs and outputs of pacing circuitry 520, which provides bradycardia pacing and anti-tachycardia pacing therapies under control of microprocessor 102 via multi-bit data/address bus 106. The operation of the pacing circuitry may correspond to that described in U.S. Pat. No. 5,177,824, issued to Keimel et al., U.S. Pat. No. 5,163,427 issued to Keimel, and U.S. Pat. No. 5,188,105, issued to Keimel, all of which are incorporated herein by reference in their entireties.

The pacer circuitry 520 includes a sense amplifier and a pacing pulse generator. Pacing circuitry 520 also includes programmable digital counters which control the basic time intervals associated with bradycardia and anti-tachycardia pacing, including the pacing escape intervals, the blanking interval during which the sense amplifier is inactive, the refractory periods during which sensed R-waves are ineffective to restart timing of the pacing escape intervals and widths of the pacing pulses. The durations of these intervals are determined by microprocessor 102, and are communicated to the pacing circuitry 520 via bus 106. Pacer timing/control circuitry also determines the amplitude of the cardiac pacing pulses, under control of microprocessor 102.

During VVI mode pacing, the escape interval counter within pacer circuitry 520 is reset upon sensing of an R-wave on electrodes 500, 502, outside of the refractory period and on timeout triggers generation of a pacing pulse, which is delivered via electrodes 500 and 502. The escape interval counter is also reset on generation of a pacing pulse. The value of the count present in the escape interval counter when reset by sensed R-waves is used to measure the duration of R—R intervals.

Switch matrix 512 is used to select which of the available electrodes are coupled to band pass amplifier 534. Selection of which two electrodes are so coupled is controlled by the microprocessor 102 via bus 106. Signals from the selected electrodes are passed through band-pass amplifier 534 and into multiplexer 532, where they are converted to multi-bit digital signals by A/D converter 108, for storage in random access memory 104 under control of direct memory address circuit 114. Preferably, a portion of random access memory 104 is configured as a looping or buffer memory which stores at least the preceding several seconds of the EGM signal. The data stored in the buffer memory may be optionally employed to perform R-wave width measurements as disclosed in co-pending U.S. patent application Ser. No. 07/867,931, filed Apr. 13, 1992 by Mader et al., incorporated herein by reference in its entirety and/or to perform the ventricular fibrillation/ventricular tachycardia discrimination function disclosed in allowed U.S. patent application Ser. No. 07/750,679 filed Aug. 27, 1991 by Bardy et al., also incorporated herein by reference in its entirety. However, the present invention may also readily be practiced in devices which do not include such functions.

Microprocessor 102 operates as an interrupt driven device, and responds to interrupts from pacer circuitry 520 corresponding to the occurrence of sensed R-waves and corresponding to the generation of cardiac pacing pulses. These interrupts are provided via data/address bus 106. Any necessary mathematical calculations to be performed by microprocessor 102 and any updating of the values or intervals controlled by pacer circuitry 520 take place following such interrupts, during the blanking intervals thereafter.

The occurrence of an R-wave is communicated to microprocessor 102 by pacing circuitry 520, via bus 106, and microprocessor 102 notes the time of its occurrence. If the width measurement function is activated, microprocessor 102 waits 100 milliseconds or other physician selected interval following the occurrence of the R-wave detect signal from the pacing circuitry 520, and thereafter transfers the most recent 200 milliseconds or other physician selected interval of digitized EGM stored in the looping or buffer memory portion of the random access memory circuit 104 to a second memory location, where the contents may be digitally analyzed to determine the width of the stored R-wave or to perform the tachycardia/fibrillation discrimination function referred to above.

The width measurement function is intended to discriminate between high rate sinus rhythms and ventricular tachycardias, and is preferably only applied to R-waves that define the endpoint of an R—R interval within the interval range indicative of tachycardia and below the interval range indicative of fibrillation. Either as a criterion for initial detection of tachycardia, or after final detection of low rate tachycardia, the device determines whether a predetermined number or proportion of a series of preceding R-waves, the widths of which have been measured, are greater than a preset threshold value (e.g. 8 of the preceding 12 measured R-waves). If the width criterion is satisfied, initial detection of tachycardia or final detection of slow ventricular tachycardia is verified. If the criterion is not met, the rhythm is diagnosed as rapid sinus rhythm and no therapy is delivered.

Similar to the width measurement function, if the discriminator function is activated, microprocessor 102 waits 100 milliseconds or other physician selected interval following the occurrence of the R-wave detect signal, and thereafter transfers the most recent 200 milliseconds or other physician selected interval of digitized EGM stored in the looping or buffer memory portion of the random access memory circuit 102 to a second memory location, where the contents may be digitally analyzed. The microprocessor 102 identifies the points in time at which the R-wave detect signal occurs and the point in time at which the 200 ms of stored ECG meets a predetermined criterion (e.g. peak slope). These two stored times, hereafter referred to as the first and second "fiducial points". The cumulative variability of the time intervals separating the occurrence of the first and second fiducial points over a series of beats is used to distinguish fibrillation from high rate ventricular tachycardia.

The microprocessor 102 also updates counts related to the R—R intervals previously sensed. The counts are incremented in response to measured R—R intervals falling within associated rate ranges. Presently available arrhythmia control devices, such as the Model 7216 and 7217 pacemaker/cardioverter/defibrillators available from Medtronic, Inc., employ programmable fibrillation detection interval ranges and tachycardia detection interval ranges which are adjacent to one another but do not overlap. In these Medtronic devices in particular, the interval range designated as indicative of ventricular fibrillation (VF) consists of intervals less than a programmable interval (FDI) and the interval range designated as indicative of ventricular tachycardia (VT) consists of intervals less than a programmable interval (TDI) and greater than or equal to FDI. R—R intervals falling within these ranges are measured and counted to provide a VT event count (VTEC) of R—R intervals falling within the tachycardia interval range and a VF event count (VFEC) of the number intervals, out of a preceding series of a predetermined number (FEB) of intervals, which fall within the fibrillation interval range. VTEC is incremented in response to R—R intervals that are greater than or equal to FDI but less than TDI, is reset to zero in response to intervals greater than or equal to TDI and is insensitive to intervals less than FDI. VTEC is compared to a programmed value (VTNID) and VFEC is compared to a corresponding programmable value (VFNID). When one of the counts equals the its corresponding programmable value, the device diagnoses the presence of the corresponding arrhythmia, i.e. fibrillation or tachycardia and delivers an appropriate therapy, e.g. anti-tachycardia pacing, a cardioversion pulse or a defibrillation pulse. In addition, the physician may optionally require that the measured R—R intervals meet a rapid onset criterion (rapid increase in rate) before VTEC can be incremented and can also optionally require that should a rate stability criterion (defined variability over a preceding series of intervals) fail to be met, VTEC will be reset to zero. This detection system has proven effective in distinguishing between fibrillation and ventricular tachycardia so that appropriate therapies may be delivered.

Onset and rate stability criteria are discussed in the article "Onset and Stability for Ventricular Tachyarrhythmia Detection in an Implantable Pacer-Cardioverter-Defibrillator" by Olson et al., published in Computers in Cardiology., Oct. 7-10, 1986, IEEE Computer Society Press, pages 167-170, also incorporated by reference in its entirety herein.

It is envisioned that the onset and stability requirements are optional in a device employing the present invention, and preferably are made available as programmable options, which may be deleted by external programmer command. If included, it is believed preferable that the onset criterion be required to met prior to initiating counting of VTEC, and that once met, the criterion will remain satisfied until detection of tachycardia termination. Thus, onset is not intended to be a detection criterion required for re-detection of tachycardia, following initial detection. The width criterion, if used, should also be understood to be useful both in initial detection of tachycardia and in re-detection of tachycardia. This reflects a presumption that following initial detection of ventricular tachycardia, absent a proven return to normal heart rhythm (termination detect), subsequent high ventricular rates should be presumed to be ventricular in origin. The stability criterion and the discriminator function may be appropriate for use both in initial detection and in re-detection.

In addition to the fibrillation and tachycardia detection criteria discussed above in connection with the Medtronic Model 7216 and Model 7217. The disclosed embodiment of the present invention also includes additional detection criteria. Initial detection of tachycardia or fibrillation detection may also be accomplished using a combined count of all intervals indicative of tachycardia or fibrillation. This combined count (VFEC+VTEC) is compared to a combined count threshold (CNID). If VTEC+VFEC is equal or greater than CNID, the device checks to see whether VFEC is at least a predetermined number (e.g. 8). If so, the device checks to determine how many of a number (e.g. 8) of the preceding intervals are greater or equal to FDI. If at least a predetermined number (e.g. 7) are greater than or equal to FDI, tachycardia is initially detected, otherwise ventricular fibrillation is initially detected. The preceding measured intervals are then examined as discussed below to determine whether the initial diagnosis of fibrillation or tachycardia should be amended to a diagnosis of fast ventricular tachycardia.

The illustrated embodiment of the present invention also defines two additional interval durations $FTDI_{max}$ and $FTDI_{min}$. $FTDI_{max}$ is an interval less than TDI and greater than FDI. $FTDI_{min}$ in is an interval less than FDI. The device also defines a third, overlapping interval range including intervals which are less than $FTDI_{max}$ and greater than or equal to $FFDI_{min}$, which intervals are taken as indicative of the possibility that a fast ventricular tachycardia is occurring. Both $FTDI_{max}$ and $FFDI_{min}$ are programmable Values, and may either or both be set equal to FDI.

Following initial detection of tachycardia or fibrillation using, the most recent series of R—R intervals (e.g. the last 8 intervals) are examined to determine how many of the intervals fall within the fast ventricular tachycardia interval range. If at least a predetermined number of intervals (e.g. 7) fall within this range, the rhythm is diagnosed as fast ventricular tachycardia. The number of intervals required to diagnose fast ventricular tachycardia may vary depending on whether ventricular fibrillation or ventricular tachycardia is initially detected. For example the device may require that 7 of the preceding 8 intervals fall within the fast ventricular tachycardia interval range to diagnose fast ventricular tachycardia, if fibrillation is initially detected. Otherwise, ventricular fibrillation would be diagnosed. Conversely, the device may only require that at least 2 of the preceding 8 intervals fall within the fast ventricular tachycardia interval range in order to diagnose fast ventricular tachycardia, if tachycardia is initially detected. Otherwise, slow ventricular tachycardia would be diagnosed.

Other detection methods for recognizing tachycardias are described in U.S. Pat. No. 4,726,380, issued to Vollmann, U.S. Pat. No. 4,880,005, issued to Pless et al., U.S. Pat. No. 4,830,006, issued to Haluska et al., U.S. Pat. No. 5,063,928, issued to Grevis et al. and U.S. Pat. No. 4,969,465, issued to Pless et al., all incorporated by reference in their entireties herein, may also be used in conjunction with the present invention, as alternatives to the detection method disclosed specifically herein. However, other detection criteria may also be measured and employed in conjunction with the present invention.

In the event that a tachyarrhythmia is detected, and an anti-tachyarrhythmia pacing regimen is desired, appropriate timing intervals for controlling generation of anti-tachycardia pacing therapies are loaded from microprocessor 524 into the pacer control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 102 employs the counters to in pacer circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 102 activates cardioversion/defibrillation control circuitry 554, which controls charging of the high voltage capacitor banks 560 via charging circuit 550, under control of high voltage charging lines 552, 553. The voltage on the high voltage capacitor banks may be monitored separately via VCAP lines 538, 539 which are passed through multiplexer 532, and, in response to reaching the same or different predetermined values set by microprocessor 102, results in generation of logic signals on CAP FULL lines 542, 543, terminating charging of the capacitor banks. Alternatively, only one capacitor bank may be employed or two capacitor banks may be employed, charged together to the same voltage. Thereafter, the timing of the defibrillation or cardioversion pulse is controlled by pacer circuitry 520. One embodiment of an appropriate system for delivery and synchronization of cardioversion and defibrillation pulses, and controlling the timing functions related to them is disclosed in more detail in allowed U.S. patent application No. 07/612,761 by Keimel, cited above. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Plesd et al., cited above, and in U.S. Pat. No. 4,375,817, issued to Engle et al., all incorporated herein by reference in their entireties may also be employed. Similarly, known circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties may also be used.

In modern pacemaker/cardioverter/defibrillators, the particular anti-tachycardia and defibrillation therapies are programmed into the device ahead of time by the physician, and a menu of therapies is typically provided. For example, on initial detection of tachycardia, an anti-tachycardia pacing therapy may be selected. On re-detection of tachycardia, a more aggressive anti-tachycardia pacing therapy may be scheduled. If repeated attempts at anti-tachycardia pacing therapies fail, a higher level cardioversion pulse therapy may be selected thereafter. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al. The present invention is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current implantable pacemaker/cardioverter/defibfillators.

In addition to varying the therapy delivered following a failed attempt to terminate a tachyarrhythmia, it is also known that adjustment of detection criteria may be appropriate. For example, adjustment may comprise reducing the number of intervals required to detect a tachyarrhythmia to allow a more rapid redetection or by changing the interval ranges to bias detection towards detection of ventricular fibrillation, for example as disclosed in U.S. Pat. No. 4,971,058, issued to Hess et al. and incorporated herein by reference in its entirety.

The disclosed embodiment of the present invention also provides the ability to select from a menu of therapies for each type of detected tachyarrhythmia, as discussed above.

The therapy menu includes cardioversion and defibrillation pulses of selectable amplitudes, as well as burst and ramp anti-tachycardia pacing modes for termination of ventricular tachycardias.

In burst pacing a series of ventricular pacing pulses is delivered at pulse intervals equal to a percentage of the average cycle length of the four R—R intervals preceding the point VTEC equals VTNID. If the burst sequence is ineffective in terminating the tachycardia, a subsequent burst sequence may be delivered, at intervals of a lesser percentage of the average cycle length of the redetected tachycardia. The physician may program the number of pulses per burst, the percentage of tachycardia cycle length, the number of sequences per burst pacing therapy, the decrement in percentage of cycle length with each successive burst and the minimum burst pulse interval. The burst pulses may be delivered in demand mode or optionally in asynchronous mode. Ramp pacing delivers a number of pacing pulses, the first pulse interval being equal to a percentage of the average cycle length of the four R—R intervals preceding the point VTEC equals VTNID, with the interval between pulses deceasing with each pulse delivered. If the ramp sequence is ineffective in terminating the tachycardia, another ramp sequence may be delivered, with an initial interval of a lesser percentage of the average cycle length of the re-detected tachycardia and subsequent intervals correspondingly reduced and with an increased number of pulses. The physician may program the number of pulses in the first ramp, the percentage of tachycardia cycle length for the first interval, the number of sequences per ramp pacing therapy, the decrement in percentage of cycle length with each successive ramp sequence and the minimum pulse interval. The pulses may be delivered in demand mode or optionally in asynchronous mode.

Each detected arrhythmia (slow VT, fast VT, fibrillation) may have, for example, up to six separate therapies programmed for use sequentially, each delivered in response to the previously delivered therapy failing to terminate the detected arrhythmia. For example, slow VT might have two ramp pacing therapies programmed followed by two burst pacing therapies. Fast VT might have only one ramp pacing therapy, followed by one burst therapy, and then by cardioversion pulses of increasing magnitude. Fibrillation will typically have four defibrillation pulse therapies of increasing amplitude.

In the present invention, selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multi-electrode, simultaneous pulse regimen or a multi-electrode sequential pulse regimen. Monophasic or biphasic pulses may be generated. One example of circuitry which may be used to perform this function is set forth in commonly assigned U.S. Pat. No. 5,163,427, cited above. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above cited references which disclose implantable cardioverters or defibrillators may also be used.

The telemetry circuitry employed to practice the present invention in the device illustrated in FIG. 1 includes telemetry timing/control circuitry 121, cyclic redundancy code circuitry 112 and uplink timing circuitry 118. The operation of these circuit blocks and their interconnection to the analog to digital converter 108, the address/data bus 106, microprocessor 102, random access memory 104 and direct memory address circuitry 114 is discussed more fully in U.S. Pat. No. 5,127,404, issued to Wyborny et al. and incorporated herein by reference in its entirety. Also employed in the telemetry function are telemetry control circuitry 124, telemetry demodulator 122 and antenna driver 120, which are discussed in more detail below.

Figure 2:
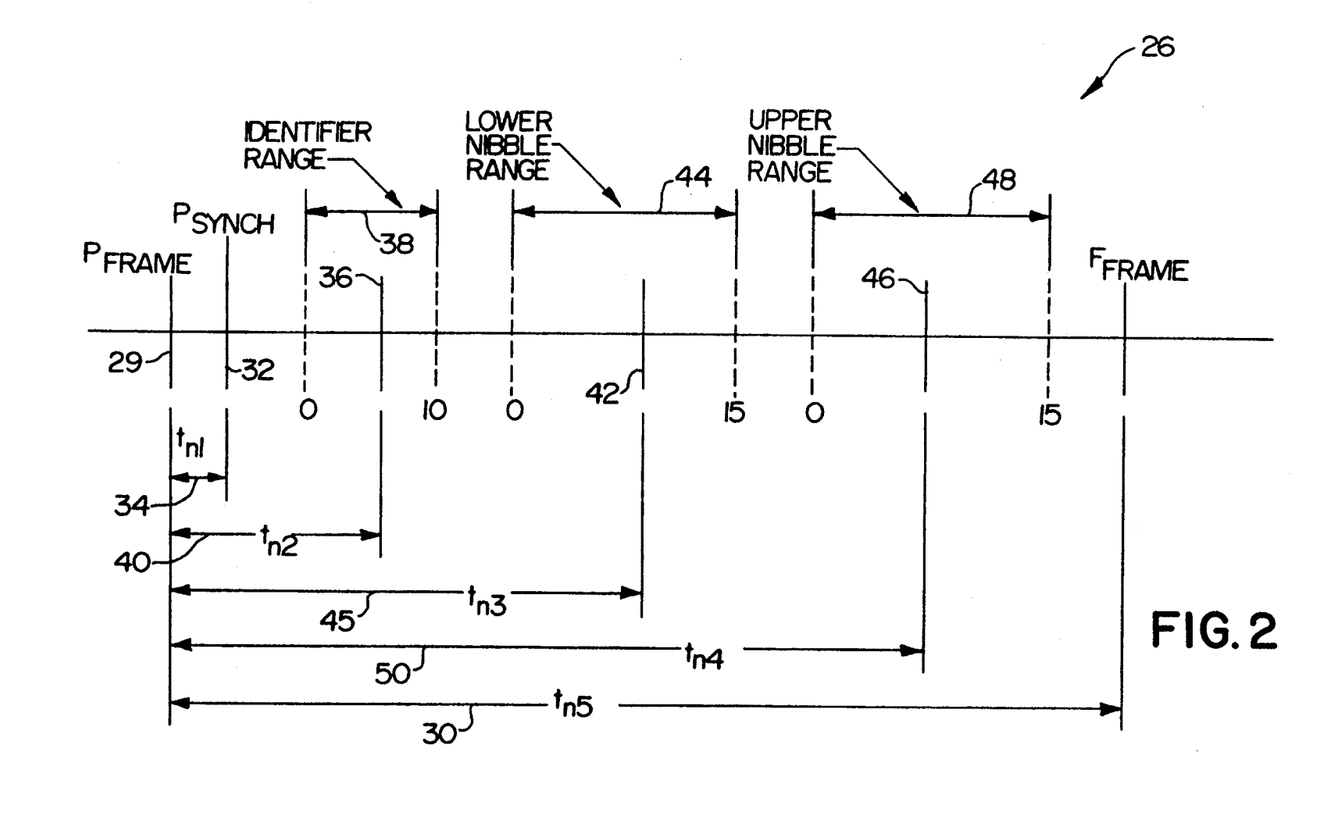
FIG. 2 is a diagram illustrating the format of the telemetry transmissions according to the present invention.
Figure 3:
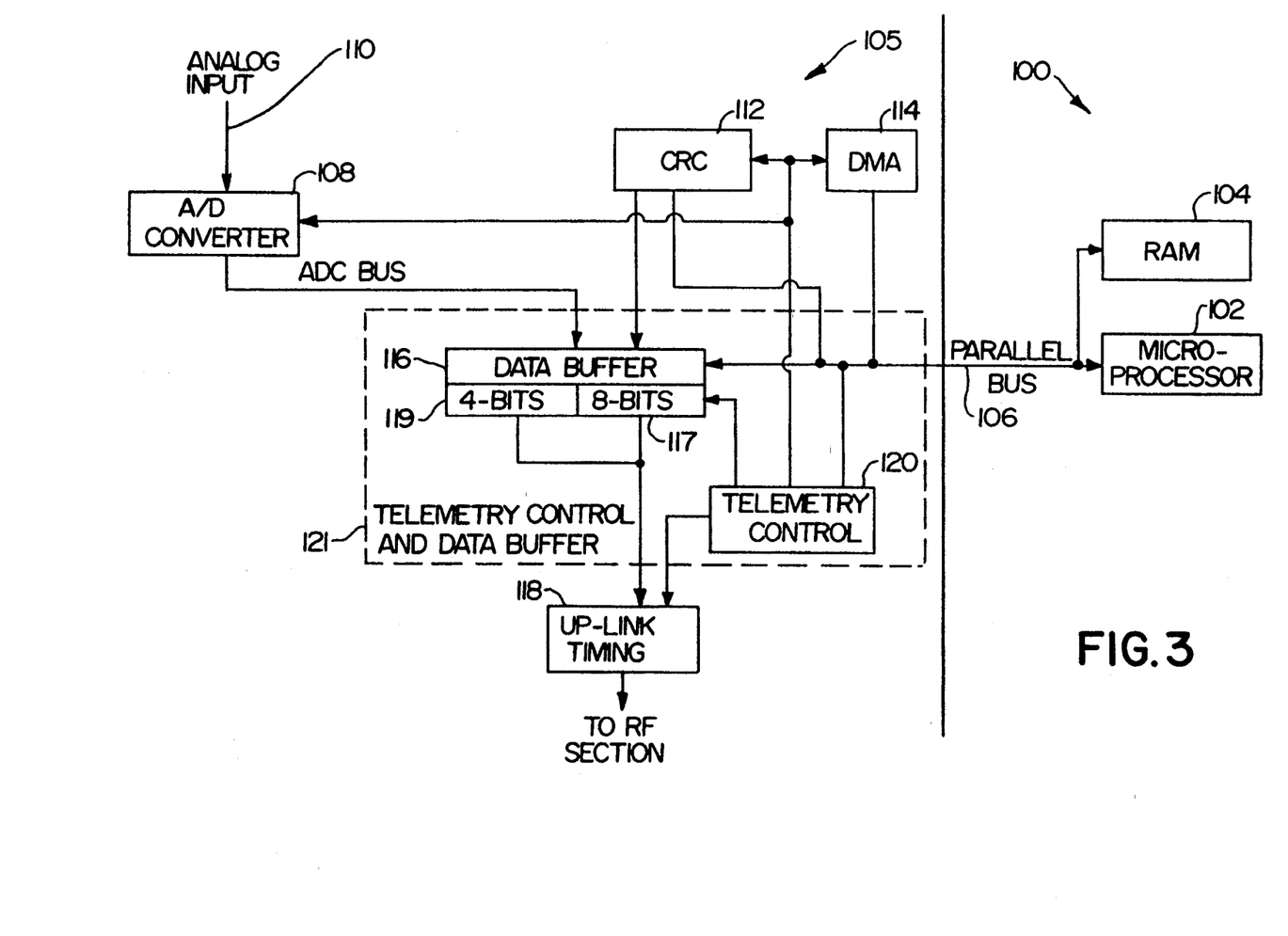
FIG. 3 is a block diagram of that portion of the device illustrated in FIG. 1 which provides telemetry transmissions according to the present invention.

FIG. 3, corresponding to FIG. 4 of the Wyborny et al. patent illustrates the telemetry timing and control circuitry 121 in more detail. Telemetry timing/control circuitry 121 controls the formatting and timing of uplink telemetry, as described in the above cited Wyborny et al. patent. Digital inputs to telemetry timing-/control circuitry 121 are provided on multi-bit bus 106. Analog input to the telemetry timing/control circuitry 121 is provided via analog to digital converter 108, which converts analog signals, such as internal electrograms via amplifier 534, the voltage of the output capacitors as indicated on line 538, and other available analog inputs on line 110 such as battery voltage, etc. into digital format for transmission. Both the output ADC bus from analog to digital converter 108 and the address/data bus 106 are provided to a 12 bit data buffer 116 within telemetry timing control circuitry 121. This buffer 116 is divided into two sections, one section 119 serving to store a four bit frame identifier code, the second section 117 serving to store a four bit upper nibble and a four bit lower nibble, which together make up a single data frame as described in above-cited Wyborny patent. Uplink timing block 118 decodes the 12 bits of data stored in data buffer 116 to produce a set of timing signals which key bursts of RF energy at the appropriate times to pulse position modulate a 175 kilohertz carrier. Uplink timing 118 also keys bursts of RF energy at fixed positions within the telemetry frame corresponding to the frame initiating pulse and the synchronizing pulse, as illustrated in FIG. 2, discussed below. Cyclic redundancy code block 112 is employed to generate the cyclic redundancy code used to provide forward error detection in uplink telemetry, and, may optionally also be employed for analyzing and verifying data received via downlink telemetry.

Returning to FIG. 1, the output of timing block 118 is provided to telemetry circuit 124 which, in response to receipt of signals from uplink timing block 118 triggers the antenna driver 120 to deliver bursts of RF energy to antenna 125. Telemetry demodulation block 122 demodulates pulse interval encoded downlink telemetry received on antenna 124, and provides to telemetry block 124, which in turn provides the serially transmitted digital data received via telemetry demodulator 122 into parallel format to delivery to microprocessor 102 via address/data bus 106.

FIG. 2 illustrates the frame format of a telemetry transmission according to the present invention, and corresponds to FIG. 2 of the above cited Wyborny et al. patent. The basic unit of the format is a frame 30, having a duration of $T_{n5}$. In the disclosed embodiment, the main timing source for generation of the telemetry frame comprises a standard 32.768 kilohertz crystal clock which provides a basic dock cycle of 30.52 microseconds. Thus, a frame comprised of 64 clock cycles extending over a fixed time interval of 1.953125 milliseconds provides a convenient frame, as the frame period is a binary multiple of the basic clock cycle. All signals within the frame comprise bursts of RF energy, triggered by uplink timing circuitry 118. The first signal is a frame signal 29 which defines the beginning of the frame. The second signal is a synchronizing signal comprising a burst 32 which is located at a time $T_{n1}$ within frame 30. The frame identifier code is positioned within the second fixed range of each frame 30. The identifier code comprises an identifier RF pulse 36 which is pulse position modulated to one of 16 available locations within the identifier range 38, and thus is a single bit hexadecimal value corresponding to the 4 bit frame identifier code stored in the first section 119 of data buffer 116 in telemetry timing and control circuitry 121 (FIG. 3). This single hexadecimal bit serves to identify the nature or type of data found within the frame.

Each frame also includes two hexadecimal bits corresponding to the two 4 bit nibbles making up the eight bit byte of data stored in the second portion 117 of data buffer 116 in telemetry timing and control circuitry 121 (FIG. 3). The telemetered data is encoded as two hexadecimal bits. The first hexadecimal bit corresponding to the four least significant bits of the byte is a pulse 42 positioned within a third fixed range of frame 30, comprising lower nibble range 44. The second hexadecimal bit, corresponding to the four most significant bits of the data byte is a pulse 46, positioned within a fourth fixed range of frame 30, upper nibble range 48. Both the upper and lower nibble ranges include 16 identifiable pulse locations within the upper and lower nibble ranges 48 and 44, respectively.

The data identifier may fall within clock cycles 9-19 following the first clock cycle of the data frame, defined by the delivery of the frame pulse 29. As indicted in the below, depending on which cycle the frame pulse falls, a variety of types of data may be indicated. Data identifier codes include a number of measured analog values including the present level of VDD (5 Hex), battery voltage measurement (6 Hex) and the difference (delta V.) between leading and trailing edges of battery voltages (7 Hex), analog EGM (8 Hex), and the voltages on two output capacitor banks (9 and A Hex). In addition, telemetry of programmed parameters (0 Hex) may be identified. Of most importance with regard to the present invention, however, are the marker (2 Hex) and marker supplement (3 Hex) data types.

Figure 4A:
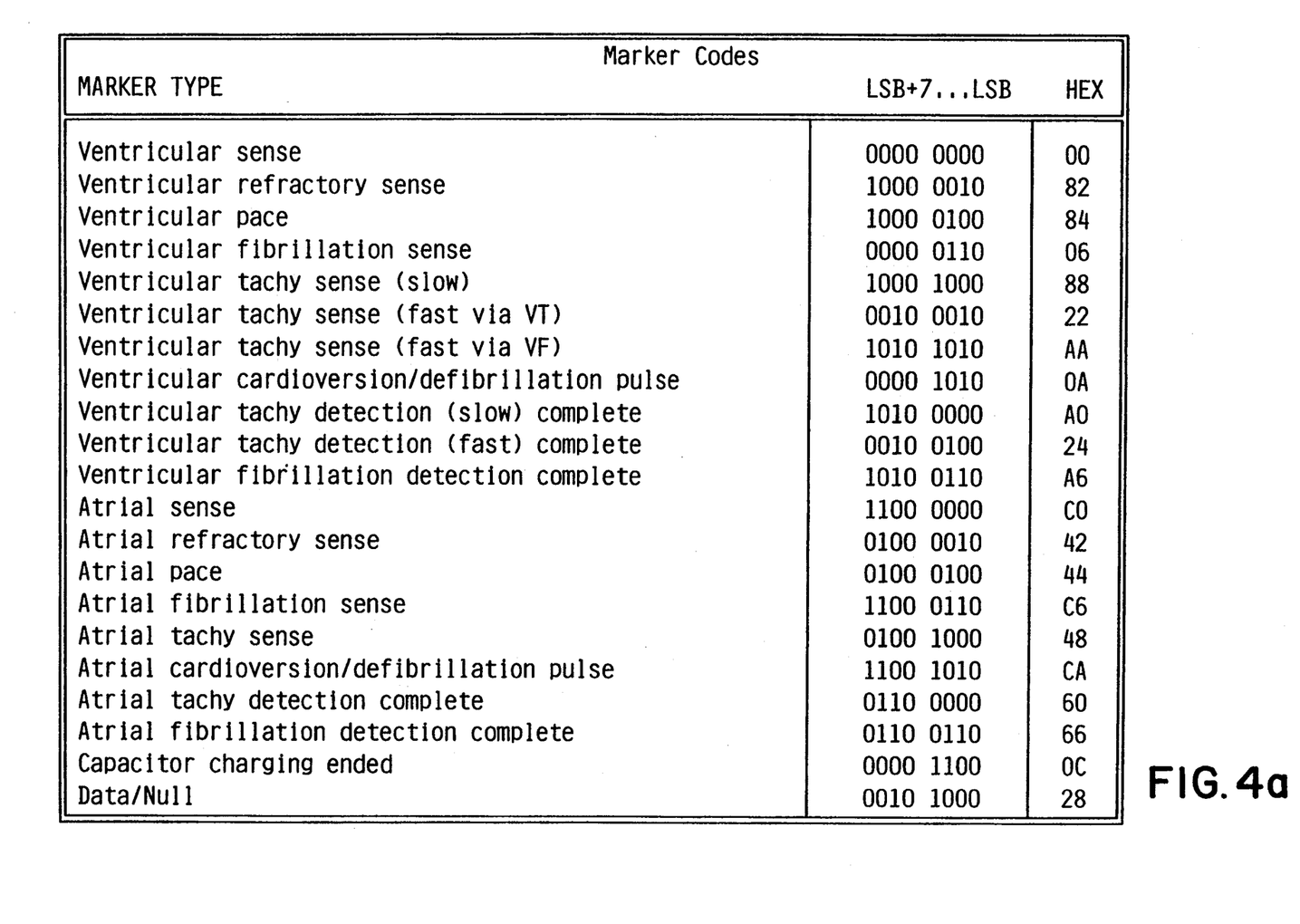
FIGS. 4a, 4b, 4c, 4d, 4e, 4f and 4g are tables listing the diagnostic parameters which are telemetered using the present invention.

The present invention, like the Medtronic Model 7216 and 7217 implantable pacemaker/cardioverter/defibrillators includes an extensive set of marker codes to be transmitted in conjunction with sensing of intrinsic depolarizations, and in conjunction with delivery of bradycardia pacing pulses, anti-tachycardia pacing pulses, as well as cardioversion and defibrillation pulses. These marker codes are listed in the table illustrated in FIG. 4a. FIG. 4a also includes reserved marker codes for use in conjunction with future devices which may also employ electrodes adapted to sense atrial heart rhythms and also includes marker designations for delivery of atrial anti-tachycardia and defibrillation therapies. On receipt by an external programmer, these marker codes are translated into graphical signals for display in conjunction with a sensed electrocardiogram, as described in U.S. Pat. No. 4,374,382, issued to Markowitz et al., incorporated herein by reference, describing the basic functioning of marker channel transmissions as presently used in many commercially available pacemakers. Graphic symbols corresponding to the marker codes are illustrated for ventricular events in FIG. 4g. Atrial events could employ the same symbols but with reversed polarity (i.e. extending below the baseline).

In addition to markers simply designating the type of individual events which occur, the present invention usefully provides marker supplement data, which is uplinked following the marker codes when the pacing interval of the device is greater than or equal to 100 milliseconds. Each block of marker supplement data is transmitted in the form of five sequential frames, each containing one byte of marker supplement information. Available information is formatted into the five marker supplement bytes, as indicted in the tables 4b, 4c, 4d, 4e and 4f, with information listed in order of priority for inclusion as part of a marker supplement transmission.

Figure 4B:
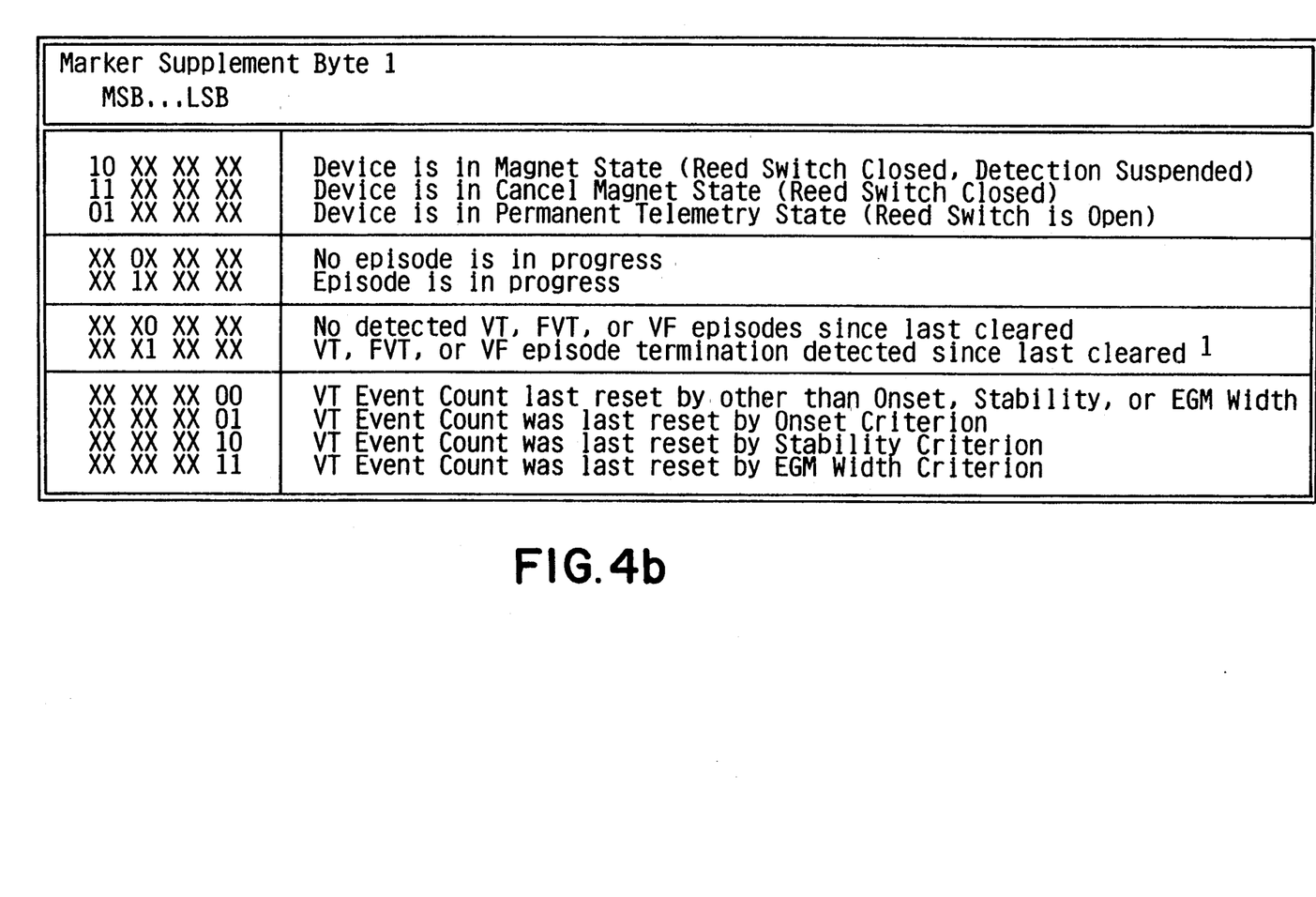

FIG. 4b illustrates the binary codes for the data bits in marker supplement frame one. These 8 bit binary bytes are encoded as two hexadecimal bits for transmission, as discussed above. Supplement data byte one is a general device status byte, broken into four two and one bit subunits. The first two bits are related to the status of the device visa vis its telemetry operation, the third bit indicates whether a tachyarrhythmia episode is in process, the fourth bit indicates whether any previous tachyarrhythmia episodes had been detected since the last time the memory was cleared, and the sixth and seventh bits indicate the circumstances under which the VT event counter was most recently reset.

Figure 4C:
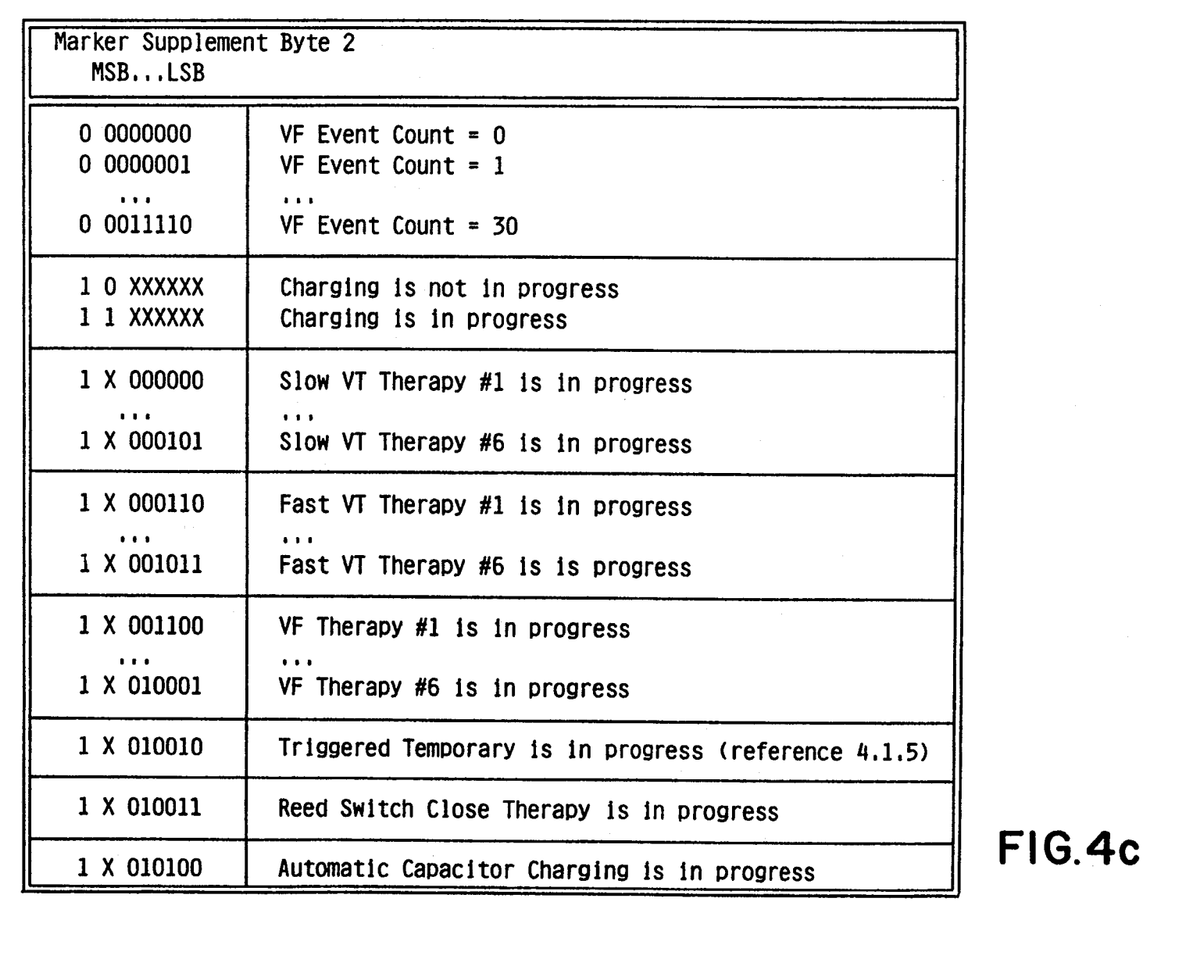

FIG. 4c illustrates marker supplement byte two, in a format corresponding to FIG. 4b. Byte two, transmitted in the second marker supplement frame, either provides information with regard to the status of the VF event counter or the status of the high voltage output capacitor charging process and the status as to whether one of a number of available therapies is being delivered. Status with regard to the VF event counter is transmitted as an alterative to information indicating the particular type of therapy presently being delivered, and/or indicating high voltage capacitor charging, as the VF event counter is disabled during charging and during delivery of anti-tachyarrhythmia therapies. As indicated in FIG. 4c, status indicators with regard to slow VT, fast VT and VF therapies are available, with the ability to designate which of six physician selected therapies for each of these three tachyarrhythmia diagnoses are being delivered. This information, in conjunction with information with regard to the therapies chosen by the physician, allows for a more complete understanding of the functioning of the device.

Figure 4D:
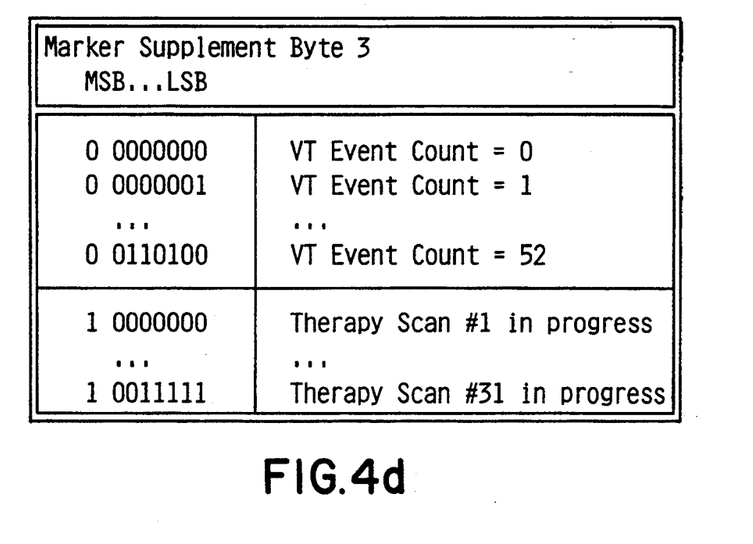

FIG. 4d illustrates marker supplement byte three, in a format corresponding to FIG. 4b. The third marker supplement byte either indicates the status of the VT event count or the VT therapy scan number presently in progress. These data types are alternatives to one another, in that the VT detection operation is disabled during delivery of an anti-tachyarrhythmia therapy. As discussed above in conjunction with the burst and ramp anti-tachycardia pacing therapies, each therapy may be repeated for a number of sequences or scans, before going on to the next therapy. In the event that such a therapy is being delivered, the third mark supplement byte will indicate which scan or sequence of the selected therapy is presently being delivered, further enhancing the physician's understanding of the therapy being delivered. Conversely, if the device is not delivering a therapy, the VT event count would accompany a VF event count in marker supplement byte two, providing a more complete understanding of the progress towards tachyarrhythmia detection.

Figure 4E:
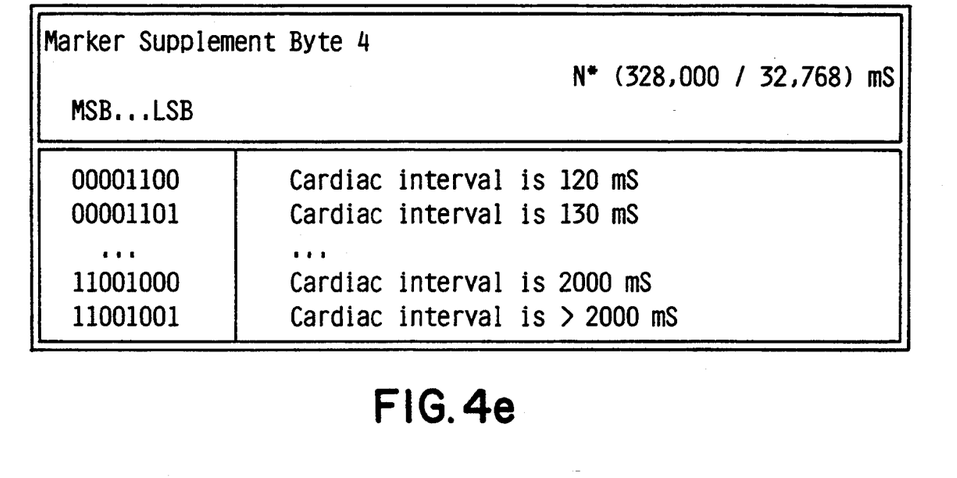

FIG. 4e illustrates marker supplement byte four, in a format corresponding to FIG. 4b. Marker supplement byte four provides a telemetered value of the measured R—R interval preceding the pacing pulse or sensed ventricular depolarization, and can be used in conjunction with the incremented values of the VT and VF event counts, to further refine the physician's understanding of the detection methodology.

Figure 4F:
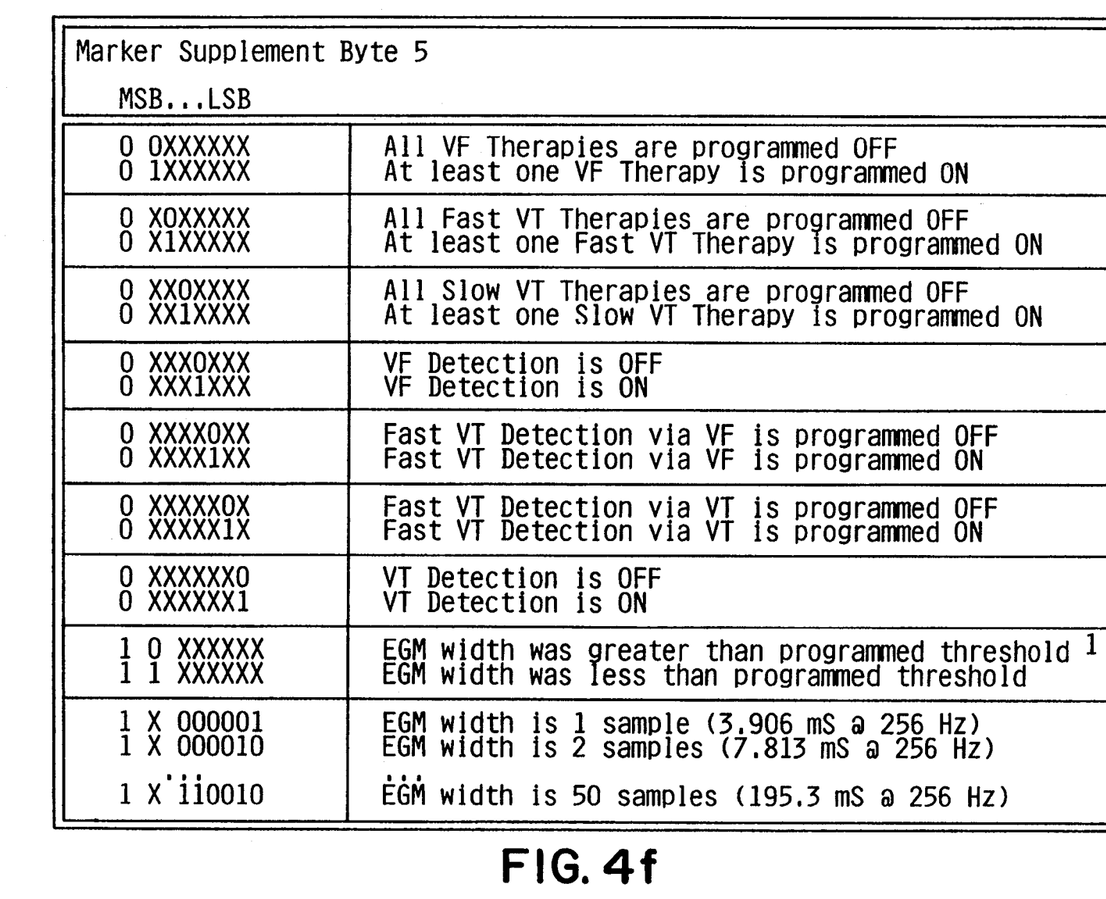
Figure 4G:
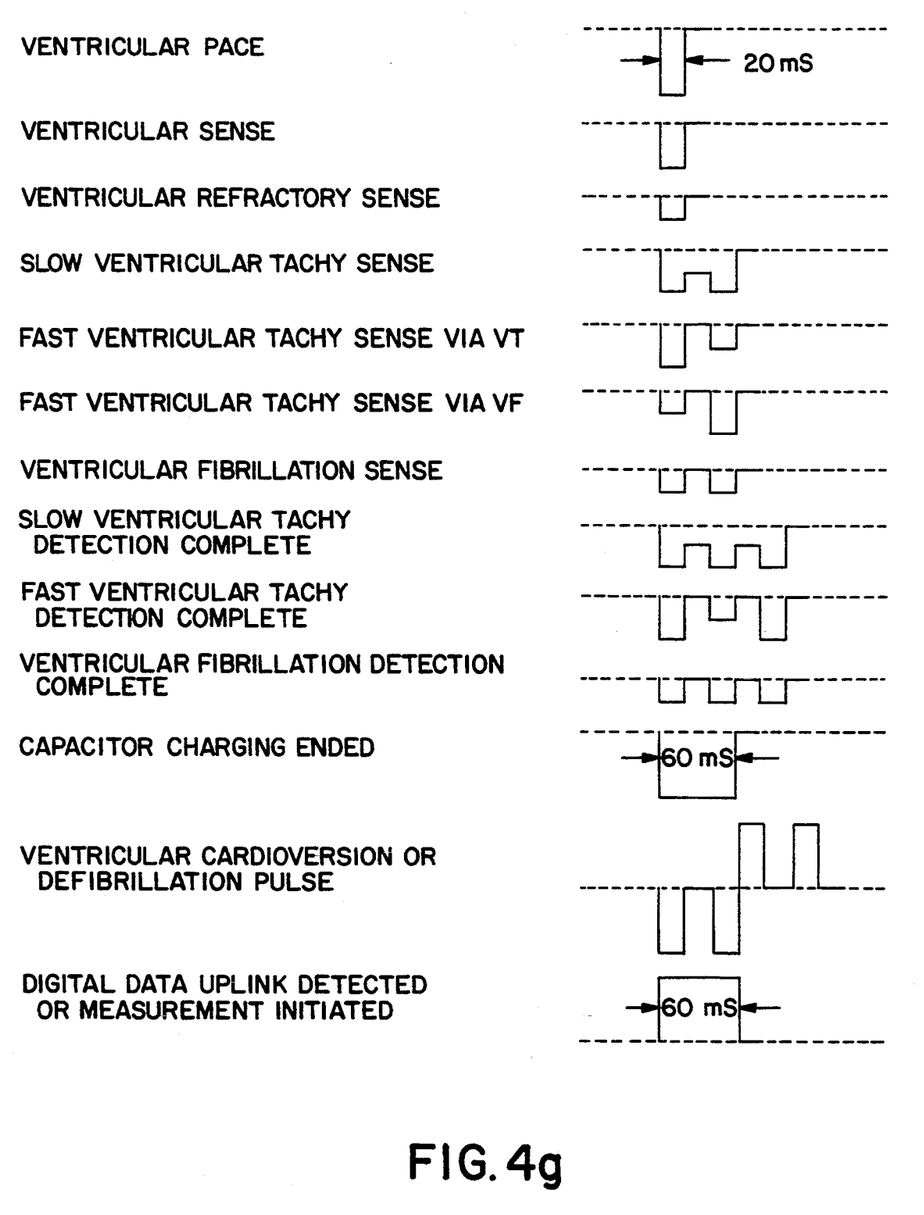

FIG. 4f illustrates marker supplement byte five, in a format corresponding to FIG. 4b. Marker supplement byte five is a status byte, when the first bit is zero, the remaining bits are used to indicate status of detection and therapy programming. The second bit indicates whether VF therapies are programmed on the third bit being used to indicate whether fast VT therapies are programmed on and the fourth bit being used to indicated whether slow VT therapies are programmed on. The fifth bit is employed to indicate whether VF detection is activated, the sixth, seventh and eighth bits being used to indicate whether fast VT detection via VF is programmed on, and whether VT detection is programmed on. With the first bit at 1, the remaining bits include information as to whether the measured electrogram width met the width criterion and, and as to the measured electrogram width.

As devices according to the present invention progress, it is anticipated that additional types of marker status information will be added, particularly in conjunction with devices which sense and treat atrial arrhythmias, and as additional detection methodologies and criteria are added. For example, in conjunction with a device as disclosed in the present application, additional marker supplement bytes which indicate whether the onset criteria has been satisfied, whether the rate stability criterion has been satisfied or whether other tachycardia detection criteria such as the width measurement and V-T/V-F discriminator functions described above have been satisfied are certainly well within the scope of the present invention. Similarly, marker status bytes indicating the status of detection of atrial arrhythmias and the status of delivery of therapies for treating atrial arrhythmias will be included in devices which have these capabilities.

While the preferred embodiment of the device takes the form of a microprocessor controlled device as illustrated in FIG. 1, in which the operation of the device is controlled by stored software, the invention may equally well be practiced in the form of a dedicated, full custom digital integrated circuit or, even in the form of an analog circuit, employing analog values as substitutes for the digital values disclosed in conjunction with the above specification.

In addition, while the preferred embodiment disclosed above takes the form of a pacemaker/cardioverter/defibrillator, the enhanced ability to telemeter information regarding detection of tachyarrhythmias and delivery of antiarrhythmia therapies provided by the present invention are also valuable and applicable to devices which are only capable of performing a subset of the various therapies discussed above in conjunction with FIG. 1.

It should further be kept in mind that while the therapies described for delivery in response to detection of the various arrhythmias discussed are all disclosed in the context of electrical therapies, it is possible that the invention may be embodied in the form of an implantable drug dispenser, wherein one or more of the antitachycardia therapies takes the form of injection of a drug locally into the heart or systemically to treat the detected arrhythmia. As such, the above disclosure should be taken merely as an example of an embodiment of the present invention, rather than limiting, when reading the claims which follow.

In conjunction with the above specification, I claim:
What is claimed is:

1. An implantable device, comprising: means for detecting heart depolarizations;
    means for measuring a parameter associated with said detected depolarizations;
    means for detecting at least first and second arrhythmias, said detecting means comprising means for defining criteria for detection of said first and second arrhythmias as a function of said measured parameter, over a series of said detected depolarizations, including means for storing an indication of the relative progress toward meeting said criteria and for updating said stored information following each detected depolarization; and
    means for telemetering information following individual ones of said detected depolarizations to an external receiver, said information comprising said updated stored information as to the relative progress toward meeting said criteria.

2. A device according to claim 1 wherein said measuring means comprises means for measuring the interval separating a said detected depolarization from a preceding detected depolarization.

3. A device according to claim 2 wherein said means for defining said criteria comprises means for defining interval ranges and for defining said criteria in the form of required counts of said measured intervals which fall into said interval ranges and wherein said means for storing an indication of the relative progress toward said meeting said criteria and for updating said stored information following each detected depolarization comprises means for storing and updating counts of said measured intervals falling within said interval ranges following each said detected depolarization.

4. An implantable anti-arrhythmia stimulator, comprising:
    means for detecting a heart arrhythmia;
    means for defining a plurality of stimulation therapies to treat said detected arrhythmia, said stimulation therapies comprising multiple stimulation pulses;
    means for selecting a said therapy;
    pulse generator means for delivering said selected therapy in response to detection of said arrhythmia; and
    means for telemetering an indication as to which of said therapies is being delivered, following individual ones of said stimulation pulses.

5. A stimulator according to claim 4 wherein said means for defining said therapies further comprises means for defining therapies each comprising a plurality of sequences of said stimulating pulses and wherein said telemetering means further comprises means for telemetering an indication of which of said plurality of sequences is being delivered, following delivery of individual ones of said stimulating pulses.

6. An implantable anti-arrhythmia stimulator, comprising:
    means for detecting heart depolarizations;
    means for measuring a parameter associated with said detected depolarizations;
    means for detecting at least first and second arrhythmias, said detecting means comprising means for defining criteria for detection of said first and second arrhythmias as a function of said measured parameter, over a series of said detected depolarizations, including means for storing an indication of the relative progress toward meeting said criteria and for updating said stored information following each detected depolarization;
    means for defining a plurality of stimulation therapies to treat said detected arrhythmias, said stimulation therapies comprising multiple stimulation pulses;
    means for selecting a said therapy;

pulse generator means for delivering said selected therapy in response to detection of said arrhythmia; and means for telemetering an indication as to which of said therapies is being delivered, following individual ones of said stimulation pulses and for telemetering information following individual ones of said detected depolarizations to an external receiver, said information comprising said updated stored information as to the relative progress toward meeting said criteria.

7. A device according to claim 6 wherein said measuring means comprises means for measuring the interval separating a said detected depolarization from a preceding detected depolarization.

8. A device according to claim 7 wherein said means for defining said criteria comprises means for defining interval ranges and for defining said criteria in the form of required counts of said measured intervals which fall into said interval ranges and wherein said means for storing an indication of the relative progress toward said meeting said criteria and for updating said stored information following each detected depolarization comprises means for storing and updating counts of said measured intervals falling within said interval ranges following each said sensed depolarization.

9. A stimulator according to claim 6 wherein said means for defining said therapies further comprises means for defining therapies each comprising a plurality of sequences of said stimulating pulses and wherein said telemetering means further comprises means for telemetering an indication of which of said 10. An implantable device, comprising:
means for detecting heart depolarizations;
means for measuring a parameter associated with said detected depolarizations;

means for detecting an arrhythmia, said detecting means comprising means for defining criteria for detection of said arrhythmias as a function of said measured parameter, over a series of said detected depolarizations, including means for storing an indication of the relative progress toward meeting said criteria and for updating said stored information following detected ones of said depolarization; and means for telemetering information following individual ones of said detected depolarizations to an external receiver, said information comprising said updated stored information as to the relative progress toward meeting said criteria. plurality of sequences is being delivered, following delivery of individual ones of said stimulating pulses.

11. A device according to claim 10 wherein said measuring means comprises means for measuring the interval separating a said detected depolarization from a preceding detected depolarization.

12. A device according to claim 11 wherein said means for defining said criteria comprises means for defining an interval range and for defining said criteria in the form of a required count of said measured intervals which fall into said interval range and wherein said means for storing an indication of the relative progress toward said meeting said criteria and for updating said stored information following each detected depolarization comprises means for storing and updating a count of said measured intervals falling within said interval range following each said detected depolarization.

* * * * *